United States Patent
Yu et al.

(10) Patent No.: US 11,318,313 B2
(45) Date of Patent: May 3, 2022

(54) RESPONSE-BASED CARDIAC RESYNCHRONIZATION THERAPY PARAMETER DETERMINATION

(71) Applicant: Cardiac Pacemakers, Inc., St. Paul, MN (US)

(72) Inventors: Yinghong Yu, Shoreview, MN (US); Krzysztof Z. Siejko, Maple Grove, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 83 days.

(21) Appl. No.: 16/845,762

(22) Filed: Apr. 10, 2020

(65) Prior Publication Data
US 2020/0324121 A1   Oct. 15, 2020

Related U.S. Application Data

(60) Provisional application No. 62/833,323, filed on Apr. 12, 2019.

(51) Int. Cl.
*A61N 1/365* (2006.01)
*A61N 1/368* (2006.01)

(52) U.S. Cl.
CPC ....... *A61N 1/36585* (2013.01); *A61N 1/3682* (2013.01); *A61N 1/3684* (2013.01); *A61N 1/36578* (2013.01)

(58) Field of Classification Search
None
See application file for complete search history.

(56) References Cited

U.S. PATENT DOCUMENTS

| | | | |
|---|---|---|---|
| 5,340,361 | A | 8/1994 | Sholder |
| 5,527,347 | A | 6/1996 | Shelton et al. |
| 6,766,197 | B1 | 7/2004 | Levine |
| 6,928,326 | B1 | 8/2005 | Levine |
| 6,973,350 | B1 | 12/2005 | Levine et al. |
| 7,079,896 | B1 | 7/2006 | Park et al. |
| 7,115,096 | B2 | 10/2006 | Siejko et al. |

(Continued)

FOREIGN PATENT DOCUMENTS

| | | |
|---|---|---|
| AU | 2018285868 B2 | 11/2020 |
| AU | 2018284386 B2 | 3/2021 |

(Continued)

OTHER PUBLICATIONS

"U.S. Appl. No. 16/007,094, Non Final Office Action dated Dec. 31, 2019", 17 pgs.

(Continued)

*Primary Examiner* — Brian T Gedeon
(74) *Attorney, Agent, or Firm* — Schwegman Lundberg & Woessner, P.A.

(57) ABSTRACT

This document discusses, among other things, systems and methods to determine a response between received cardiac electrical information from a subject, such as a time of a P wave, and received cardiac acceleration information of the subject, such as a time of a first heart sound (S1) or a second heart sound (S2), across a set of stimulation signals provided to the subject at different AVD intervals, and determining one or more cardiac resynchronization therapy (CRT) parameters using an inflection point of the determined response.

20 Claims, 6 Drawing Sheets

(56) References Cited

U.S. PATENT DOCUMENTS

| | | | |
|---|---|---|---|
| 7,972,275 | B2 | 7/2011 | Siejko et al. |
| 8,048,001 | B2 | 11/2011 | Patangay et al. |
| 8,121,685 | B2 | 2/2012 | Ding et al. |
| 8,160,700 | B1 | 4/2012 | Ryu et al. |
| 9,220,905 | B2 | 12/2015 | Munsterman et al. |
| 9,345,410 | B2 | 5/2016 | Thakur et al. |
| 9,433,792 | B2 | 9/2016 | Rosenberg et al. |
| 9,622,664 | B2 | 4/2017 | An et al. |
| 9,968,266 | B2 | 5/2018 | An et al. |
| 11,040,207 | B2 | 6/2021 | Ternes et al. |
| 2003/0204145 | A1 | 10/2003 | Manolas |
| 2004/0106960 | A1* | 6/2004 | Siejko .......... A61N 1/3684 607/17 |
| 2005/0131476 | A1 | 6/2005 | Kim et al. |
| 2005/0137632 | A1 | 6/2005 | Ding et al. |
| 2006/0224198 | A1 | 10/2006 | Dong et al. |
| 2006/0282000 | A1 | 12/2006 | Zhang et al. |
| 2007/0179542 | A1 | 8/2007 | Prakash et al. |
| 2007/0191892 | A1 | 8/2007 | Mullen et al. |
| 2009/0287106 | A1 | 11/2009 | Zhang et al. |
| 2010/0069988 | A1 | 3/2010 | Ding et al. |
| 2010/0305646 | A1 | 12/2010 | Schulte et al. |
| 2011/0196440 | A1 | 8/2011 | Koh |
| 2012/0157797 | A1 | 6/2012 | Zhang et al. |
| 2012/0158088 | A1 | 6/2012 | Kramer et al. |
| 2013/0030489 | A1 | 1/2013 | Munsterman et al. |
| 2013/0131750 | A1 | 5/2013 | Stadler et al. |
| 2013/0268017 | A1 | 10/2013 | Zhang et al. |
| 2014/0276163 | A1 | 9/2014 | Thakur et al. |
| 2014/0277233 | A1 | 9/2014 | Ghosh |
| 2016/0051823 | A1 | 2/2016 | Maile et al. |
| 2016/0144192 | A1 | 5/2016 | Sanghera et al. |
| 2016/0220357 | A1 | 8/2016 | Anand et al. |
| 2016/0310733 | A1 | 10/2016 | Sheldon et al. |
| 2017/0106191 | A1 | 4/2017 | Pei |
| 2017/0239472 | A1* | 8/2017 | Zhang .......... A61N 1/37264 |
| 2018/0361150 | A1 | 12/2018 | Ternes et al. |
| 2018/0361161 | A1 | 12/2018 | Ternes et al. |
| 2018/0361162 | A1 | 12/2018 | Ternes et al. |
| 2019/0298903 | A1 | 10/2019 | Gillberg et al. |
| 2020/0178850 | A1 | 6/2020 | Thakur et al. |
| 2020/0324120 | A1 | 10/2020 | Yu et al. |

FOREIGN PATENT DOCUMENTS

| | | |
|---|---|---|
| CN | 110740780 A | 1/2020 |
| CN | 110769893 A | 2/2020 |
| CN | 110769894 A | 2/2020 |
| CN | 113453625 A | 9/2021 |
| JP | H10-504754 A | 5/1998 |
| JP | 2008-538981 A | 11/2008 |
| JP | 2012-527957 A | 11/2012 |
| JP | 2020-523139 A | 8/2020 |
| JP | 2020-523152 A | 8/2020 |
| JP | 2020-523153 A | 8/2020 |
| JP | 6936345 B2 | 8/2021 |
| JP | 6936346 B2 | 8/2021 |
| WO | WO-2018189671 A1 | 10/2018 |
| WO | WO-2018231939 A1 | 12/2018 |
| WO | WO-2018231996 A1 | 12/2018 |
| WO | WO-2018232004 A1 | 12/2018 |
| WO | WO-2019144058 A1 | 7/2019 |
| WO | WO-2020/123487 A1 | 6/2020 |

OTHER PUBLICATIONS

"U.S. Appl. No. 16/007,094, Response filed Mar. 31, 2020 to Non Final Office Action dated Dec. 31, 2019", 14 pgs.

"U.S. Appl. No. 16/007,494, Non Final Office Action dated Feb. 24, 2020", 16 pgs.

"International Application Serial No. PCT/US2018/037269, International Preliminary Report on Patentability dated Dec. 26, 2019", 8 pgs.

"International Application Serial No. PCT/US2018/037269, International Search Report dated Aug. 31, 2018", 4 pgs.

"International Application Serial No. PCT/US2018/037269, Written Opinion dated Aug. 31, 2018", 6 pgs.

"International Application Serial No. PCT/US2018/037350, International Preliminary Report on Patentability dated Dec. 26, 2019", 9 pgs.

"International Application Serial No. PCT/US2018/037350, International Search Report dated Nov. 16, 2018", 6 pgs.

"International Application Serial No. PCT/US2018/037350, Invitation to Pay Additional Fees and Partial Search Report dated Sep. 20, 2018", 8 pgs.

"International Application Serial No. PCT/US2018/037350, Written Opinion dated Nov. 16, 2018", 7 pgs.

"International Application Serial No. PCT/US2018/037359, International Preliminary Report on Patentability dated Dec. 26, 2019", 8 pgs.

"International Application Serial No. PCT/US2018/037359, International Search Report dated Sep. 18, 2018", 5 pgs.

"International Application Serial No. PCT/US2018/037359, Written Opinion dated Sep. 18, 2018", 8 pgs.

Daubert, Jean-Claude, et al., "2012 EHRA/HRS expert consensus statement on cardiac resynchronization therapy in heart failure: implant and follow-up recommendations and management", Heart Rhythm, vol. 9, No. 9, Sep. 2012, pp. 1524-1576.

Ellenbogen, Kenneth A., et al., "Primary Results From the SmartDelay Determined AV Optimization: A Comparison to Other AV Delay Methods Used in Cardiac Resynchronization Therapy (SMART-AV) Trial: A Randonmized Trial Comparing Empirical Echocardiography-Guiled, and Algorithmic . . . ", Circulation, http://circ.ahajournals.org/content/early/2010/11/12/CIRCULATIONAHA.110.992552, Nov. 12, 2010, 19 pages.

"U.S. Appl. No. 16/007,094, Advisory Action dated Oct. 27, 2020", 4 pgs.

"U.S. Appl. No. 16/007,094, Examiner interview Summary dated Sep. 25, 2020", 3 pgs.

"U.S. Appl. No. 16/007,094, Final Office Action dated Jul. 24, 2020", 18 pgs.

"U.S. Appl. No. 16/007,094, Non-Final Office Action dated Jun. 11, 2021", 15 pgs.

"U.S. Appl. No. 16/007,094, Non-Final Office Action dated Sep. 1, 2021", 17 pgs.

"U.S. Appl. No. 16/007,094, Response filed Sep. 24, 2020 to Final Office Action dated Jul. 24, 2020", 13 pgs.

"U.S. Appl. No. 16/007,494, Examiner Interview Summary dated May 15, 2020", 3 pgs.

"U.S. Appl. No. 16/007,494, Examiner Interview Summary dated Nov. 19, 2020", 4 pgs.

"U.S. Appl. No. 16/007,494, Non-Final Office Action dated Sep. 4, 2020", 17 pgs.

"U.S. Appl. No. 16/007,494, Notice of Allowance dated Feb. 18, 2021", 9 pgs.

"U.S. Appl. No. 16/007,494, Response filed May 26, 2020 to Non-Final Office Action dated Feb. 24, 2020", 11 pgs.

"U.S. Appl. No. 16/007,494, Response filed Dec. 7, 2020 to Non-Final Office Action dated Sep. 4, 2020", 11 pgs.

"U.S. Appl. No. 16/007,784, Advisory Action dated Jun. 9, 2021", 3 pgs.

"U.S. Appl. No. 16/007,784, Examiner Interview Summary dated Jun. 2, 2021", 2 pgs.

"U.S. Appl. No. 16/007,784, Final Office Action dated Mar. 31, 2021", 10 pgs.

"U.S. Appl. No. 16/007,784, Non-Final Office Action dated Aug. 19, 2020", 18 pgs.

"U.S. Appl. No. 16/007,784, Notice of Allowance dated Jul. 29, 2021", 8 pgs.

"U.S. Appl. No. 16/007,784, Response filed Jun. 1, 2021 to Final Office Action dated Mar. 31, 2021", 12 pgs.

"U.S. Appl. No. 16/007,784, Response filed Oct. 27, 2020 to Non-Final Office Action dated Aug. 19, 2020", 13 pgs.

"U.S. Appl. No. 16/709,382, Non-Final Office Action dated Sep. 14, 2021", 18 pgs.

(56) References Cited

OTHER PUBLICATIONS

"U.S. Appl. No. 16/845,730, Non-Final Office Action dated Sep. 1, 2021", 11 pgs.
"Australian Application Serial No. 2018283029, First Examination Report dated May 7, 2020", 4 pgs.
"Australian Application Serial No. 2018283029, Response filed Apr. 7, 2021 to Subsequent Examiners Report dated Oct. 14, 2020", 2 pgs.
"Australian Application Serial No. 2018283029, Response filed Aug. 20, 2020 to First Examination Report dated May 7, 2020", 16 pgs.
"Australian Application Serial No. 2018283029, Subsequent Examiners Report dated Oct. 14, 2020", 4 pgs.
"Australian Application Serial No. 2018284386, First Examination Report dated May 11, 2020", 4 pgs.
"Australian Application Serial No. 2018284386, Response filed Aug. 14, 2020 to First Examination Report dated May 11, 2020", 2 pgs.
"Australian Application Serial No. 2018284386, Subsequent Examiners Report dated Sep. 4, 2020", 4 pgs.
"Australian Application Serial No. 2018285868, First Examination Report dated May 6, 2020", 4 pgs.
"Australian Application Serial No. 2018285868, Response filed Sep. 9, 2020 to First Examination Report dated May 6, 2020", 7 pgs.
"European Application Serial No. 18738066.2, Response to Communication Pursuant to Rules 161 and 162 filed Jul. 28, 2020", 3 pgs.
"European Application Serial No. 18738068.8, Response to Communication Pursuant to Rules 161 and 162 filed Jul. 28, 2020", 16 pgs.
"European Application Serial No. 18737095.2, Response filed Aug. 4, 2020 to Communication pursuant to Rules 161(1) and 162 EPC dated Jan. 30, 2020", 16 pgs.
"International Application Serial No. PCT/US2019/065455, International Preliminary Report an Patentability dated Jun. 24, 2021", 9 pgs.
"International Application Serial No. PCT/US2019/065455, International Search Report dated Apr. 2, 2020", 6 pgs.
"International Application Serial No. PCT/US2019/065455, Written Opinion dated Apr. 2, 2020", 7 pgs.
"Japanese Application Serial No. 2019-569278, Final Notification of Reasons for Refusal dated Nov. 17, 2020", (w/ English Translation), 12 pgs.
"Japanese Application Serial No. 2019-569278, Response filed Feb. 16, 2021 to Final Notification of Reasons far Refusal dated Nov. 17, 2020", w/ English Claims, 9 pgs.
"Japanese Application Serial No. 2019-569384, Office Action dated Nov. 24, 2020", (w/ English Translation), 12 pgs.
"Japanese Application Serial No. 2019-569384,Response filed Feb. 22, 2021 Office Action dated Nov. 24, 2020", (w/ English Translation of Claims), 10 pgs.
"Japanese Application Serial No. 2019-569386, Office Action dated Nov. 24, 2020", (w/ English Translation), 10 pgs.
Japanese Application Serial No. 2019-569386, Response Filed Feb. 19, 2021 to Office Action dated Nov. 24, 2020, (w/ English Translation of Claims), 9 pgs.

* cited by examiner

RESPONSE-BASED CARDIAC RESYNCHRONIZATION THERAPY PARAMETER DETERMINATION

CLAIM OF PRIORITY

This application claims the benefit of priority under 35 U.S.C. § 119(e) of U.S. Provisional Patent Application Ser. No. 62/833,323, filed on Apr. 12, 2019, which is herein incorporated by reference in its entirety.

TECHNICAL FIELD

This document relates generally to medical devices, and more particularly, but not by way of limitation, to systems, devices, and methods for response-based cardiac resynchronization therapy (CRT) parameter determination.

BACKGROUND

Heart failure (HF) is a reduction in the ability of the heart to deliver enough blood to meet bodily needs, affecting over five million patients in the United States alone. HF patients commonly have enlarged heart with weakened cardiac muscles, resulting in reduced contractility and poor cardiac output of blood. Typical signs of HF include: pulmonary congestion; edema; difficulty breathing; etc.

Ambulatory medical devices (AMDs), including implantable medical devices (IMDs), wearable medical devices, etc., have been used to monitor heart failure patients and manage heart failure in an ambulatory setting. Some AMDs may include sensors to sense physiological signals from a patient, and detect worsening heart failure, such as heart failure decompensation. Frequent patient monitoring and early detection of worsening heart failure may help improve patient outcome. Identification of patient at an elevated risk of future heart failure events may help provide timely treatment and prevent or reduce hospitalization. Identifying and safely managing the patients at risk of worsening heart failure can avoid unnecessary medical interventions, hospitalization, and reduce healthcare cost.

An AMD may include a pulse generator and electrical circuitry configured to electrically stimulate a heart or other excitable tissue, to help restore or improve the cardiac performance, or to correct cardiac arrhythmias. One example of the electrostimulation therapy is cardiac resynchronization therapy (CRT). CRT can include biventricular (BiV) pacing or synchronized left ventricle (LV)-only pacing, and may be indicated for heart failure patients with moderate to severe symptoms and ventricular dyssynchrony. CRT keeps the LV and right ventricle (RV) pumping synchronously by sending electrical stimuli to both the LV and RV. The synchronized stimulation may improve heart pumping efficiency and increase blood flow in some heart failure patients. CRT can decrease hospitalization and morbidity associated with heart failure or worsening heart failure (WHF), as well as improvements in quality of life (QoL).

SUMMARY

This document discusses, among other things, systems and methods to determine a response between received cardiac electrical information from a subject, such as a time of a P wave, and received cardiac acceleration information of the subject, such as a time of a first heart sound (S1) or a second heart sound (S2), across a set of stimulation signals provided to the subject at different AVD intervals, and determining one or more cardiac resynchronization therapy (CRT) parameters using an inflection point of the determined response.

Example 1 is a system, comprising: a signal receiver circuit configured to receive cardiac electrical information of a subject and cardiac acceleration information of the subject in response to a set of stimulation signals at different atrioventricular delay (AVD) intervals; and an assessment circuit configured to: determine a response between the received cardiac electrical information and the received cardiac acceleration information across the set of stimulation signals at the different AVD intervals; determine an inflection point of the determined response; and determine a cardiac resynchronization therapy (CRT) parameter for the subject using the determined inflection point.

In Example 2, the subject matter of Example 1 optionally includes wherein the set of stimulation signals at different AVD intervals includes at least three stimulation signals at different AVD intervals in separate cardiac cycles.

In Example 3, the subject matter of any one or more of Examples 1-2 optionally include wherein the system is a medical-device system, comprising: a cardiac stimulation circuit configured to generate the set of stimulation signals to be delivered to the subject, the stimulation signal including a left ventricular (LV) stimulation signal at an AVD interval; and a stimulation control circuit configured to adjust the AVD interval of the set of stimulation signals across different cardiac cycles, wherein the assessment circuit is configured to determine the inflection point using the determined response across the set of stimulation signals at the different AVD intervals and a threshold.

In Example 4, the subject matter of any one or more of Examples 1-3 optionally include wherein the assessment circuit is configured to determine the inflection point using a characteristic of the determined response.

In Example 5, the subject matter of any one or more of Examples 1-4 optionally include multiple electrodes configured to provide stimulation to a heart of the subject using the stimulation signal from the cardiac stimulation circuit and to detect the cardiac electrical information of the subject; and an accelerometer configured to detect the cardiac acceleration information of the subject, wherein the signal receiver circuit is configured to receive the cardiac electrical information from at least two of the multiple electrodes and the cardiac acceleration information from the accelerometer.

In Example 6, the subject matter of any one or more of Examples 1-5 optionally include wherein the received cardiac electrical information includes a time of a P wave of the subject, wherein the received cardiac acceleration information includes a time of a heart sound of the subject, wherein the assessment circuit is configured to determine the response between the time of the P wave and the time of the heart sound, and wherein, to determine the CRT parameter using the determined inflection point, the assessment circuit is configured to determine an AVD value at the determined inflection point.

In Example 7, the subject matter of Example 6 optionally includes wherein the time of the heart sound includes a time of a first heart sound (S1), and wherein the assessment circuit is configured to determine the response between the time of the P wave and the time of the S1 (P-S1).

In Example 8, the subject matter of any one or more of Examples 6-7 optionally include wherein the time of the heart sound includes a time of a second heart sound (S2), and wherein the assessment circuit is configured to determine the response between the time of the P wave and the time of the S2 (P-S2).

In Example 9, the subject matter of any one or more of Examples 1-8 optionally include wherein the CRT parameter includes an AVD.

In Example 10, the subject matter of any one or more of Examples 1-9 optionally include wherein the assessment circuit is configured to determine the CRT parameter using the determined inflection point and at least one of a determined QRS width or one or more of an interval between an atrial activation and a right ventricular activation (ARV) or an interval between an atrial activation and a left ventricular activation (ALV).

Example 11 is a method, comprising: receiving, using a signal receiver circuit, cardiac electrical information of a subject and cardiac acceleration information of the subject in response to a set of stimulation signals at different atrioventricular delay (AVD) intervals; determining, using an assessment circuit, a response between the received cardiac electrical information and the received cardiac acceleration information across the set of stimulation signals at the different AVD intervals; determining, using the assessment circuit, an inflection point of the determined response; and determining, using the assessment circuit, a cardiac resynchronization therapy (CRT) parameter for the subject using the determined inflection point.

In Example 12, the subject matter of Example 11 optionally includes wherein the set of stimulation signals at different AVD intervals includes at least three stimulation signals at different AVD intervals in separate cardiac cycles.

In Example 13, the subject matter of any one or more of Examples 11-12 optionally include generating, using a cardiac stimulation circuit, the set of stimulation signals to be delivered to the subject, the stimulation signal including a left ventricular (LV) stimulation signal at an AVD interval; and adjusting, using a stimulation control circuit, the AVD interval of the set of stimulation signals across different cardiac cycles, wherein determining the inflection point comprises using the response across the set of stimulation signals at the different AVD intervals and a threshold.

In Example 14, the subject matter of any one or more of Examples 11-13 optionally include wherein determining the inflection point comprises using a characteristic of the determined response.

In Example 15, the subject matter of any one or more of Examples 11-14 optionally include providing, using multiple electrodes, stimulation to a heart of the subject using the stimulation signal from the cardiac stimulation circuit; detecting, using at least two of the multiple electrodes, cardiac electrical information of the subject; and detecting, using an accelerometer, the cardiac acceleration information of the subject, wherein receiving the cardiac electrical information comprises from at least two of the multiple electrodes and receiving the cardiac acceleration information comprises from the accelerometer.

In Example 16, the subject matter of any one or more of Examples 11-15 optionally include wherein determining the response between the received cardiac electrical information and the received cardiac acceleration information comprises determining a response between a time of a P wave and a time of a heart sound, and wherein, to determine the CRT parameter using the determined inflection point, the assessment circuit is configured to determine an AVD value at the determined inflection point.

In Example 17, the subject matter of Example 16 optionally includes wherein the time of the heart sound includes a time of a first heart sound (S1), and the response incudes a response between the time of the P wave and the time of the S1 (P-S1).

In Example 18, the subject matter of any one or more of Examples 16-17 optionally include wherein the time of the heart sound includes a time of a second heart sound (S2), and the response includes a response between the time of the P wave and the time of the S2 (P-S2).

In Example 19, the subject matter of any one or more of Examples 11-18 optionally include wherein the CRT parameter includes an AVD.

In Example 20, the subject matter of any one or more of Examples 11-19 optionally include wherein determining the CRT parameter includes using the determined inflection point and at least one of a determined QRS width or one or more of an interval between an atrial activation and a right ventricular activation (ARV) or an interval between an atrial activation and a left ventricular activation (ALV).

In Example 21, subject matter (e.g., a system or apparatus) may optionally combine any portion or combination of any portion of any one or more of Examples 1-20 to comprise "means for" performing any portion of any one or more of the functions or methods of Examples 1-20, or at least one "non-transitory machine-readable medium" including instructions that, when performed by a machine, cause the machine to perform any portion of any one or more of the functions or methods of Examples 1-20.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
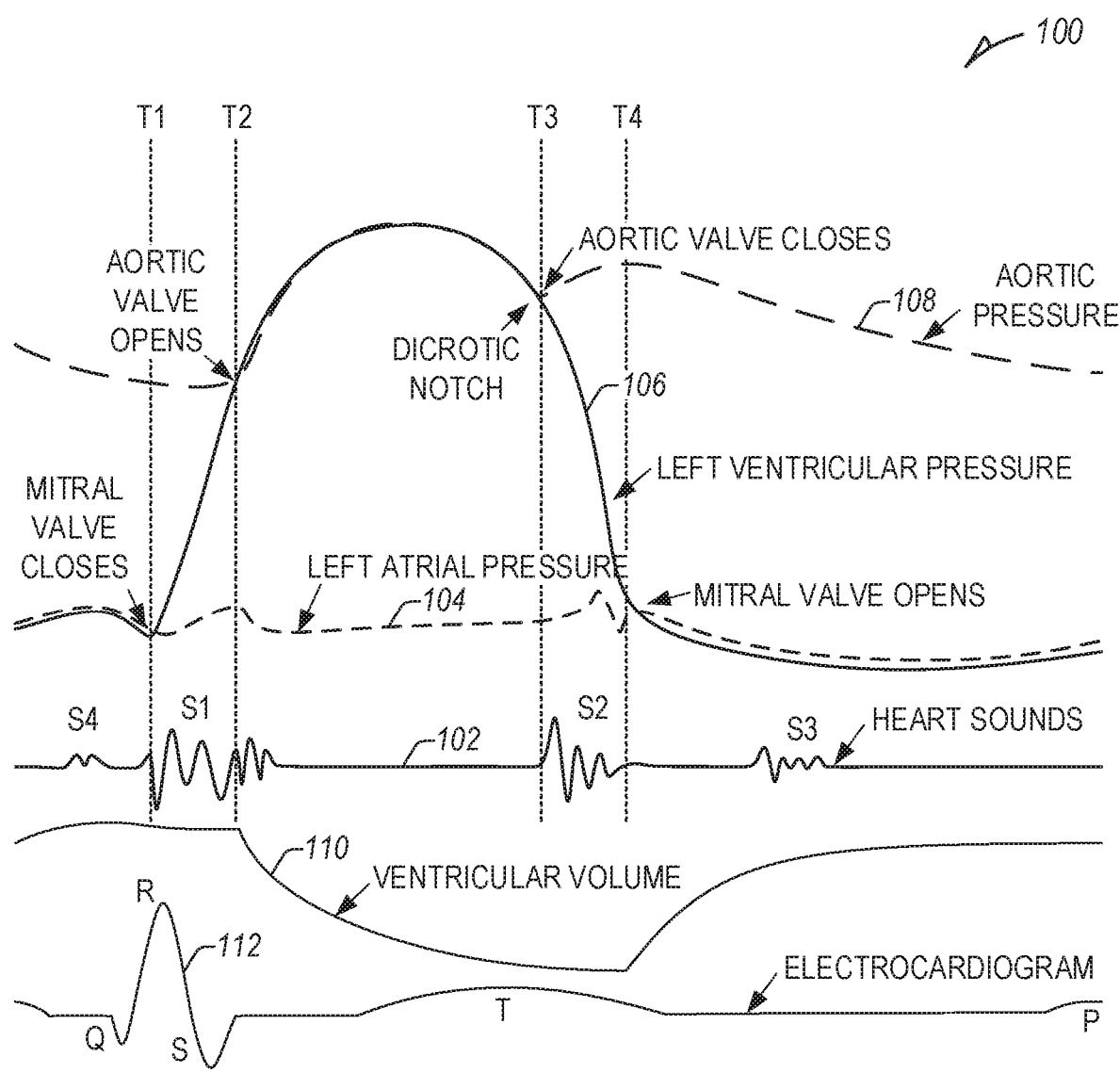
FIG. 1 illustrates an example relationship between physiologic signals of a subject.

Heart sounds are recurring mechanical signals associated with cardiac vibrations or accelerations from blood flow through the heart or other cardiac movements with each cardiac cycle and can be separated and classified according to activity associated with such vibrations, accelerations, movements, pressure waves, or blood flow. Heart sounds include four major features: the first through the fourth heart sounds. The first heart sound (S1) is the vibrational sound made by the heart during closure of the atrioventricular (AV) valves, the mitral valve and the tricuspid valve, at the beginning of systole. The second heart sound (S2) is the vibrational sound made by the heart during closure of the aortic and pulmonary valves at the beginning of diastole. The third and fourth heart sounds (S3, S4) are related to filling pressures of the left ventricle during diastole. Valve closures and blood movement and pressure changes in the heart can cause accelerations, vibrations, or movement of the cardiac walls that can be detected using an accelerometer or a microphone, providing an output referred to herein as cardiac acceleration information. In other examples, valve movement can be detected directly via imaging technologies such as echocardiography and magnetic resonance imaging (MRI) or by intracardiac impedance plethysmography.

Heart sounds can be used to detect or improve detection of a number of physiologic conditions, including, for example, acute physiologic events, such as one or more abnormal cardiac rhythms (e.g., atrial fibrillation, atrial flutter, cardiac mechanical dyssynchrony, etc.), or chronic physiologic events (e.g., ischemia, heart failure, etc.). For example, heart failure can be detected using heart sounds. For example, an index of third heart sound (S3) information can be used to monitor heart failure, such as disclosed in the commonly assigned Siejko et al. U.S. Pat. No. 7,115,096, titled "Third Heart Sound Activity Index for Heart Failure Monitoring", herein incorporated by reference in its entirety. A HF risk score can be determined, and WHF detection can be adjusted using a measured physiological parameter of a sensed S3 heart sound, such as disclosed in the commonly assigned An et al. U.S. Pat. No. 9,968,266, titled "Risk Stratification Based Heart Failure Detection Algorithm", herein incorporated by reference in its entirety. A physiologic indicator, such as a HF status indication, can be determined using a trend of a determined heart sound characteristic following a transition from an elevated activity level to a less elevated activity level, such as disclosed in the commonly assigned Thakur et al. U.S. Pat. No. 9,345,410, titled "Diagnostic and Optimization using Exercise Recovery Data", herein incorporated by reference in its entirety.

Aspects of CRT may include selection of an AV delay (AVD), or selection of one or more electrodes from a plurality of available electrodes (e.g., of a quadripolar lead having four electrodes, etc.), etc. Measurements of an electrocardiogram (ECG) can be used to optimize an AVD for a patient, for example, using patient information or a combination of patient and population information. For example, a pacing site or vector for delivering stimulation energy can be selected using timing information from one or more cardiac electrical features or parameters (e.g., a P wave, a Q wave, an R wave, a QRS complex, a T wave, etc.) and one or more other cardiac electrical or mechanical features (e.g., LV activation, RV activation, etc.), such as a Q-LV interval, etc., or timings of one or more other cardiac electrical parameters (e.g., RV-LV interval, etc.), such as disclosed in the commonly assigned Ternes et al. U.S. patent application Ser. No. 16/007,094, titled "Systems and Methods for Dynamic Control of Heart Failure Therapy", herein incorporated by reference in its entirety.

A number of subjects are non-responders to cardiac resynchronization therapy (CRT), in certain examples, up to 30-50% or more, such as due to AV block (e.g., impaired conduction between the atria and the ventricles), atrial fibrillation (AF), etc. The present inventors have recognized, among other things, that heart sound response characterization can be used to determine or select an AVD interval for a subject, such as in combination with one or more other parameters (e.g., RV-LV, QRS width, etc.). Heart sound response characterization can improve cardiac resynchronization therapy (CRT), such as by providing patient-specific hemodynamic response in determining one or more CRT parameters, especially in patients where intrinsic AV intervals (ARV, ALV) cannot be applied, such as due to AV block or one or more other conditions, thereby reducing the number of non-responders to CRT therapy.

In an example, such patient-specific hemodynamic response can be in contrast to hemodynamic response information based on empirical derivation of response characteristics from an acute dataset of responses (e.g., a medical study, etc.). Heart sound timing response characterization, such as disclosed herein, can be used to more-reliably determine CRT parameters, providing more robust optimization and control of cardiac activation synchrony, improving patient hemodynamic response using patient-specific information.

In certain examples, such improvements may reduce the demand for subsequent CRT adjustment, resulting in fewer missed beats (e.g., loss of capture, etc.), improved patient outcomes, and reduced processing and power requirements. Such improvements may increase sensitivity or specificity of parameter determination, increasing data collection and storage efficiency, providing a more robust patient monitoring system, in certain examples, using less storage or data processing than existing systems. Moreover, improved detection of conditions or detection of additional conditions in sophisticated, regulatory-compliant medical systems, components, or machinery may increase the efficiency of medical system resources, improving the functioning of modern regulated technological systems and methods not capable of being performed or managed by generic computers, components, or machinery.

FIG. 1 illustrates an example relationship 100 between physiologic information, including heart sounds 102 (first, second, third, and fourth heart sounds (S1, S2, S3, and S4)), left atrial pressure 104, left ventricular pressure 106, aortic pressure 108, ventricular volume 110 (e.g., left ventricular volume), and an electrocardiogram (ECG) 112.

At a first time (T1), a mitral valve closes, marking a rise in left ventricular pressure 106, and the start of the first heart sound (S1) and systole, or ventricular contraction. At a second time (T2), an aortic valve opens, marking a rise in aortic pressure 108, a drop in ventricular volume 110, and continuing S1. S1 is caused by closure of the atrioventricular (AV) valves, including the mitral and tricuspid valves, and can be used to monitor heart contractility.

At a third time (T3), an aortic valve closes, causing a dicrotic notch in the aortic pressure 108 and the second heart sound (S2), and marking the end of systole, or ventricular contraction, and the beginning of diastole, or ventricular relaxation. S2 can be used to monitor blood pressure. At a fourth time (T4), the mitral valve opens, the left atrial pressure 104 drops, and the ventricular volume 110 increases. An abrupt halt of early diastolic filling can cause the third heart sound (S3), which can be indicative of (or an early sign of) heart failure (HF). Vibrations due to atrial kick can cause the fourth heart sound (S4), which can be used to monitor ventricular compliance.

Systolic time intervals, such as pre-ejection period (PEP) or left ventricular ejection time (LVET) can be indicative of clinically relevant information, including contractility, arrhythmia, Q-T prolongation (with electrogram (EGM) information), etc. The PEP can be measured from a Q wave of an EGM to the time of the aortic valve opening, T2 in FIG. 1. The LVET can include a time between the aortic valve opening, T2, and the aortic valve closing, T3. In other examples, one or more systolic time intervals can be detected and used to detect physiologic information of a subject (e.g., PEP/LVET, one or more mechanical, electrical, or mechanical-electrical time intervals, etc.).

In certain examples, one or more periods or measurements can be made and correlated to specific pacing parameters to adjust CRT. For example, a time interval between the P wave to S1 (P-S1) can be measured for a range of atrioventricular delay (AVD) values and compared to intrinsic values (e.g., intrinsic P-S1 values, or one or more other value, such as a time interval between the P wave and an R wave (P-R), etc.).

Figure 2:
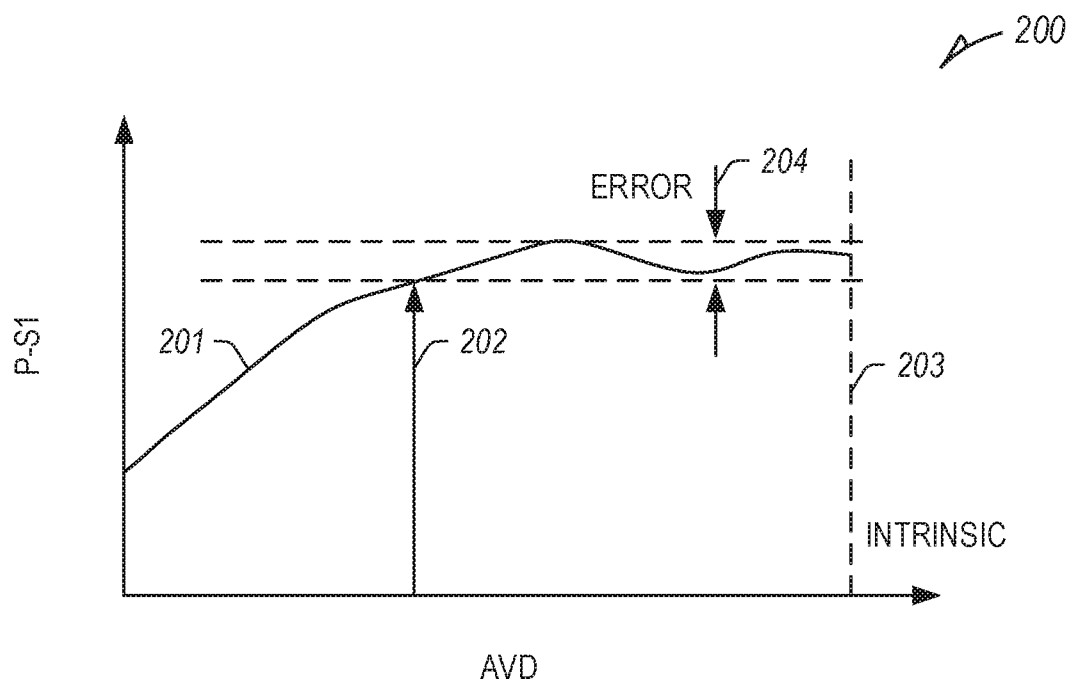
FIGS. 2-3 illustrate an example relationships between a time interval between a P wave and a subsequent S1 (P-S1) for a range of AVD values.

FIG. 2 illustrates an example relationship 200 between a time interval between a P wave and a subsequent S1 (P-S1) for a range of AVD values, including a response curve 201. In an example, multiple AVD values (e.g., a range of AVD values) can be scanned for a specific pacing configuration. An inflection point 202 can be determined where paced activation begins to approach (e.g., within a measurement error threshold, etc.) or overtake intrinsic activation 203. In certain examples, the AVD can be set to the value of the inflection point 202. In certain examples, the threshold can be dependent on the variation in determined response, detected noise in the physiologic information, or using a shape of the response. In other examples, the shape of the response can be filtered to account for variation, etc.

Inflection points, specifically with regards to heart sounds, and particularly, the onset of S1, can be difficult to determine, as many physiologic signals, such as the S1 heart sound, may not be detected with a singular rising edge. For example, as illustrated in FIG. 1, S1 can have many rising and falling edges. Accordingly, some amount of measurement error 204 (e.g., S1 onset measurement error) can be determined and applied. In certain examples, the inflection point 202 can be determined with respect to the applied measurement error 204.

In addition to onset measurement error, many physiologic signals commonly have left and right-side components. Differences in patient information (e.g., a loud S4, low signal amplitudes) can also make determination of specific events difficult, impacting detection and measurements. If the AVD is too short, the start of LV contractility may be caused by pre-excitation, resulting in sub-optimal contractility reinforcement. If the AVD is too long, the start of LV contractility may be caused completely by intrinsic conduction, with LV contractile reinforcement too late to affect S1 onset, resulting in a sub-optimal rate of ventricular pressure change (dP/dt). An optimal AVD results in mechanical fusion, aligning paced and mechanical (e.g., intrinsic) activation, such as indicated by S1 onset timing. In an example, mechanical fusion, with respect to AVD, can include the longest AVD where a paced P-S1 interval is shorter than an intrinsic P-S1 interval.

The present inventors have recognized, among other things, that an inflection point or a shape of a response curve, or a response function, of a cardiac acceleration timing interval (e.g., a heart sound timing interval), such as a P-S1 interval, a P-S2 interval, or one or more other intervals between a cardiac electrical signal parameter and a cardiac acceleration parameter (e.g., a heart sound parameter) or two cardiac acceleration parameters, etc., can be used to determine or select an AVD for subsequent CRT stimulation to be delivered to a subject. In an example, an inflection point of a P-S1 or a P-S2 response curve across a set of AVD values can be used to determine or select the AVD for subsequent CRT stimulation to be delivered to the subject. Moreover, the inflection point can be used, such as in contrast with one or more other measured parameters, to determine or select the AVD, such as to provide an AVD at or near the point of mechanical fusion.

For CRT patients with normal AV delay conduction (e.g., determined by or received from a clinician or otherwise detected or measured, etc.), the AVD can be computed or measured as a function of one or more of an AVD at the inflection point, an intrinsic RV-LV interval, an intrinsic QRS width, or one or more other parameters or subset of such parameters. For example:

$$AVD = K1(AVD_{INFL}) + K2(RV-LV) + K3; \quad (1)$$

$$AVD = K1(AVD_{INFL}) + K2(QRS_{WIDTH}) + K3; \text{ or} \quad (2)$$

$$AVD = K1(AVD_{INFL}) + K2(RV-LV) + K3(QRS_{WIDTH}) + K4, \quad (3)$$

where K1, K2, K3, and K4 are variables, $AVD_{INFL}$ is an AVD at the inflection point of a cardiac acceleration timing interval, RV-LV is an interventricular delay (e.g., a time interval between activation of the right and left ventricles), and $QRS_{WIDTH}$ is a width of the QRS complex, etc.

For CRT patients with AV block or AF (e.g., determined by or received from a clinician or otherwise detected or measured, etc.), the AVD can be computed or measured as a function of one or more of an AVD at the inflection point, a paced RV-LV interval (e.g., an interval between an RV pace and a subsequent LV sense, etc.), a paced QRS width (e.g., RV paced), or one or more other parameters or subset of such parameters. For example:

$$AVD = K1(AVD_{INFL}) + K2(RV-LV_{PACED}) + K3; \quad (4)$$

$$AVD = K1(AVD_{INFL}) + K2(QRS_{PACED}) + K3; \text{ or} \quad (5)$$

$$AVD = K1(AVD_{INFL}) + K2(RV-LV_{PACED}) + K3(QR-S_{PACED}) + K4, \quad (6)$$

where K1, K2, K3, and K4 are variables, $AVD_{INFL}$ is an AVD at the inflection point of a cardiac acceleration timing interval, $RV-LV_{PACED}$ is a paced interventricular delay, and $QRS_{PACED}$ is a width of the QRS complex, such as in response to an RV pace, etc.

In certain examples, the shape of the response curve itself can be characterized and used to select or determine one or more parameters. As used herein, parameters may refer to a pacing parameter (e.g., an amplitude, timing (such as AVD, etc.)), pacing site or electrode (e.g., LV1, LV2, etc.), or pacing mode or configuration (e.g., biventricular pacing, left-ventricular-only (LV-only) pacing, multi-site pacing, single-site pacing, etc.). In an example, a curvature value can be used to estimate a strength of a dP/dt response, such as a percent change in dP/dt (% dP/dt). The curvature value, optionally in combination with one or more other parameters (e.g., RV-LV interval, QRS width, etc.) can be used to select or determine one or more parameters.

Determining one or more CRT parameters can include, among other things, determining if the subject is a responder or a non-responder to a particular CRT parameter or CRT therapy using a determined response curve (e.g., using one or more characteristics of a determined response curve). Determining one or more CRT parameters can include determining or selecting one or more pacing vector, pacing electrode, or pacing mode using the determined response curve. In other examples, determining one or more CRT parameters can include confirming or rejecting one or more CRT parameters using determined response curves of the one or more CRT parameters. In an example, an initial priority of a set of candidate CRT parameters can be determined, and the set of candidate CRT parameters can be tested in order of priority until one of the candidate CRT parameters are confirmed using the determined response curve of the respective candidate CRT parameter.

Figure 3:
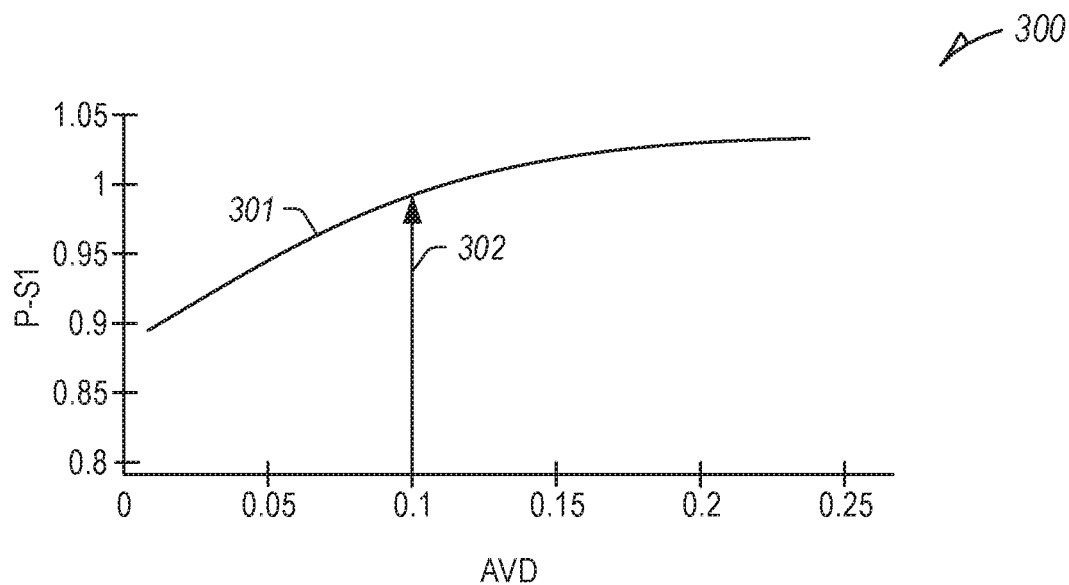

FIG. 3 illustrates an example relationship 300 between a time interval between a P wave and a subsequent S1 (P-S1) for a range of AVD values, including a response curve 301. Like in FIG. 2, multiple AVD values can be scanned for a specific pacing configuration. Multiple P-S1 measurements can be made at different AVD values (e.g., more than 2), and the response curve 301 can be fit to the results, such as using one or more curve-fitting techniques or equations (e.g., a quadratic or polynomial least-squares fit, second degree polynomial, third- or higher-degree polynomial, etc.). Similar curve-fitting can be employed for other curves described herein, with multiple measurements made at different AVD values, and a curve fit to the results. An inflection point 302 can be determined where paced activation begins to approach or overtake intrinsic activation, such as within a threshold or some characterization of the response (e.g., a rate of change, a slowing rate of change, an approach within a threshold, such as measurement error, etc.).

Figure 4:
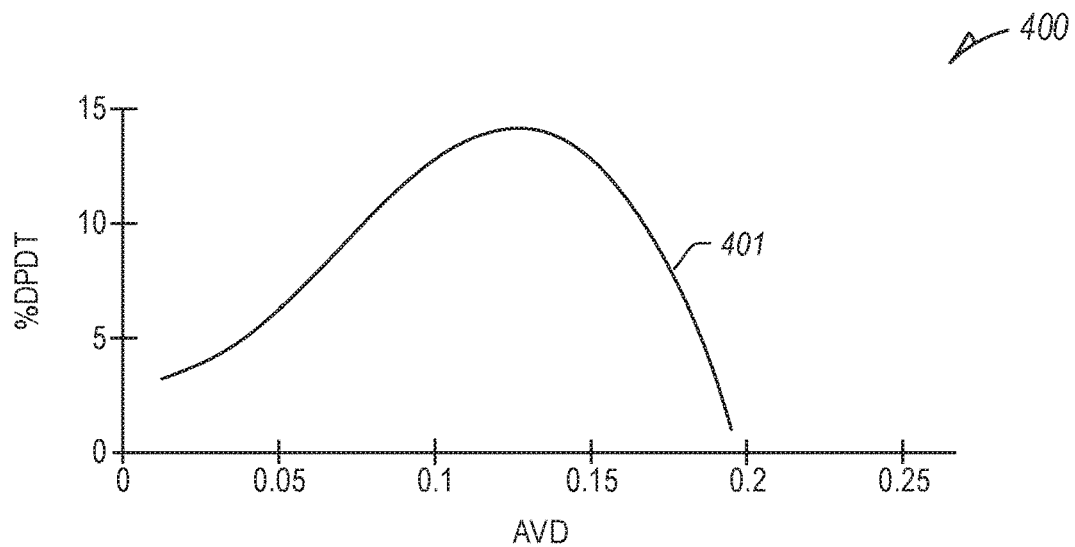
FIGS. 4-5 illustrates an example relationship between rates of ventricular pressure change (dP/dt) for a range of AVD values.

FIG. 4 illustrates an example relationship 400 between a rate of ventricular pressure change (dP/dt) (e.g., left ventricular pressure change), specifically a percent change in dP/dt (% dP/dt) in contrast to an intrinsic dP/dt (e.g., without ventricular pacing), for a range of AVD values, including in a response curve 401. Multiple dP/dt measurements can be made at different AVD values (e.g., more than 2), and the response curve 401 can be fit to the results. Different AVD provide different dP/dt values. Such specific values in FIG. 4 are illustrative and may vary in other examples.

Figure 5:
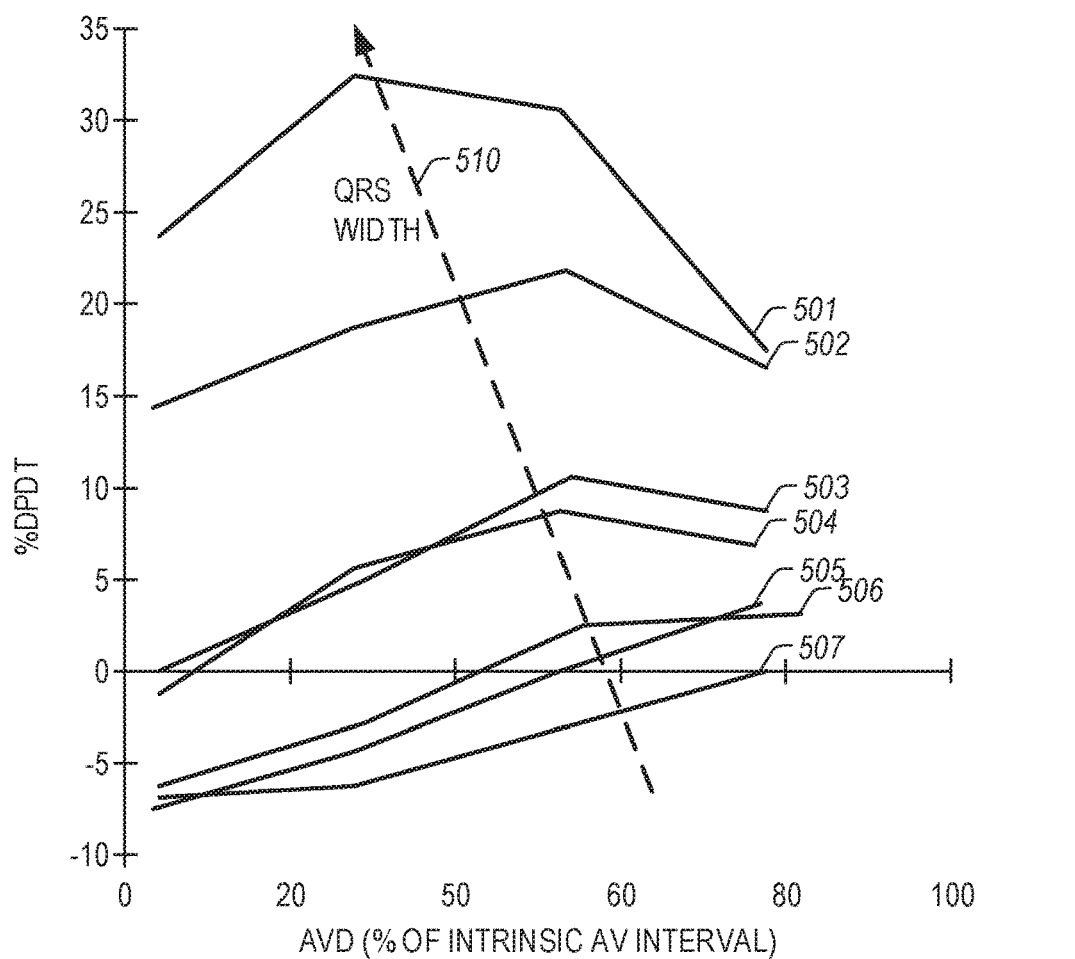

FIG. 5 illustrates an example relationship 500 between a rate of ventricular pressure change (dP/dt) (e.g., left ventricular pressure change), specifically a percent change in dP/dt (% dP/dt) in contrast to an intrinsic dP/dt (e.g., without ventricular pacing), for a range of AVD values, for multiple pacing configurations 501-507 having different QRS widths. FIG. 5 illustrates that, generally, dP/dt response increases as the QRS width increases, while the optimal AVD, such as determined using inflection points, etc., decreases. A QRS width line 510 illustrates the generally increasing QRS width for the multiple pacing configurations 501-507, at or near the optional AVD for the multiple pacing configurations 501-507.

In the example of FIG. 5, a first pacing configuration 501 has a QRS width greater than 180 ms; a second pacing configuration 502 has a QRS width between 170 and 180 ms; a third pacing configuration 503 has a QRS width between 160 and 170 ms; a fourth pacing configuration 504 has a QRS width between 150 and 160 ms; a fifth pacing configuration 505 has a QRS width between 140 and 150 ms; a sixth pacing configuration 506 has a QRS width between 130 and 140 ms; and a seventh pacing configuration 507 has a QRS width between 120 and 130 ms;

In an example, determination of an inflection point can help identify a better dP/dt response for different pacing protocols (e.g., vein location pairs, etc.), or in certain examples, can be used, such as in combination with an RV-LV interval or one or more other parameters (e.g., ARV, ALV, QRS width, etc.) to determine pacing site or one or more other parameter selections, such as illustrated in Table 1.

TABLE 1

| Example Performance | |
|---|---|
| Feature set | $R^2$ |
| ARV, ALV | .39 |
| ARV, ALV, $AVD_{INFL}$ | .44 |
| ARV, ALV, $AVD_{INFL}$, QRS width | .49 |
| $AVD_{INFL}$ | .29 |
| QRS width, $AVD_{INFL}$ | .42 |

The example values in Table 1 are illustrative and indicate performance improvements using an AVD at an inflection point in combination with one or more other parameters. The different feature sets include combinations of detection features or parameters. R-squared ($R^2$) is a statistical measure of variance of the data with a highest value (best fit) of 1 and a lowest value (worst fit) of 0. For each feature set, combinations including the AVD at the inflection point provide variance performance improvements. In an example, for patients with AV block, such that intrinsic ARV or ALV may not be determined, the performance of the feature set including QRS width and AVD at the inflection point is notable, in certain examples, improving CRT optimization for traditional non-responders.

Figure 6:
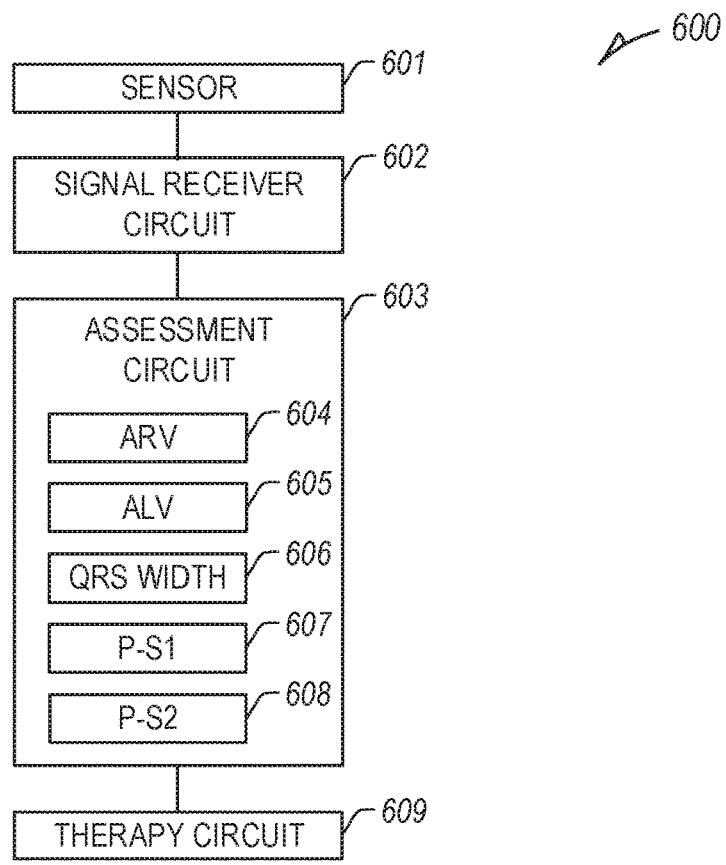
FIG. 6 illustrates an example system including a signal receiver circuit and an assessment circuit.

FIG. 6 illustrates an example system (e.g., a medical-device system, etc.) 600 including a signal receiver circuit 602 and an assessment circuit 603. The signal receiver circuit 602 can be configured to receive subject information, such as physiologic information of a subject, a patient (or a group of subjects or patients) from one or more sensors, such as sensor 601. The assessment circuit 603 can be configured to receive information from the signal receiver circuit 602, and to determine one or more parameters (e.g., composite physiologic parameters, stratifiers, one or more pacing parameters, etc.), such as described herein.

The assessment circuit 603 can be configured to provide an output to a user, such as to a display or one or more other user interface, the output including a score, a trend, an alert, or other indication. In other examples, the assessment circuit 603 can be configured to provide an output to another circuit, machine, or process, such as a therapy circuit 609 (e.g., a CRT therapy circuit, etc.), etc., to control, adjust, or cease a therapy of a medical device, a drug delivery system, etc., or otherwise alter one or more processes or functions of one or more other aspects of a medical-device system, such as one or more CRT parameters, etc. In an example, the therapy circuit 609 can include one or more of a stimulation control circuit and a cardiac stimulation circuit. In other examples, the therapy circuit 609 can be controlled by the assessment circuit 603, or one or more other circuits, etc.

In an example, the assessment circuit 603 can include one or more sub-circuits or processes configured to detect or measure one or more specific parameters, including, for example, one or more of an: interval between an atrium (e.g., RA) and an RV (ARV), such as using an ARV circuit 604; an interval between an atrium (e.g., RA) and an LV (ALV), such as using an ALV circuit 605; a QRS width, such as using a QRS width circuit 606; one or more characteristics of a P-S1 response (e.g., an inflection point), such as using a P-S1 circuit 607; one or more characteristics of a P-S2 response (e.g., an inflection point), such as using a P-S2 circuit 608; etc. In an example, a processing circuit, or one or more other components of an AMD or one or more other medical-system components, can be configured to detect or measure one or more of the parameters described herein, such as using information detected from one or more sensors, etc.

In an example, one or more aspects of the example system 600 can be a component of, or communicatively coupled to, an ambulatory medical device (AMD). AMDs can be configured to monitor, detect, or treat various cardiac conditions associated with a reduced ability of a heart to sufficiently deliver blood to a body, such HF, arrhythmias, hypertension, dyssynchrony, etc. AMDs can include a single device or a plurality of medical devices or monitors implanted in a subject's body or otherwise positioned on or about the subject to monitor subject physiologic information of the subject, such as using one or more sensors (e.g., the sensor 601), the physiologic information including one or more of heart sounds, respiration (e.g., respiration rate, tidal volume, etc.), impedance (e.g., thoracic impedance, cardiac impedance, etc.), pressure (e.g., blood pressure), cardiac activity (e.g., heart rate, electrocardiogram (ECG) information, etc.), physical activity, posture, plethysmography, or one or more other physiologic parameters of a subject, or to provide electrical stimulation or one or more other therapies or treatments to optimize or control contractions of the heart.

In an example, the sensor 601 can include one or more of: a respiration sensor configured to receive respiration information (e.g., a respiration rate (RR), a respiration volume (tidal volume), etc.); an acceleration sensor (e.g., an accelerometer, a microphone, etc.) configured to receive cardiac acceleration information (e.g., cardiac vibration information, pressure waveform information, heart sound information, endocardial acceleration information, acceleration information, activity information, posture information, etc.); an impedance sensor (e.g., intrathoracic impedance sensor, transthoracic impedance sensor, etc.) configured to receive impedance information, a cardiac sensor configured to receive cardiac electrical information; an activity sensor configured to receive information about a physical motion (e.g., activity, steps, etc.); a posture sensor configured to receive posture or position information; a pressure sensor configured to receive pressure information; a plethysmograph sensor (e.g., a photoplethysmography sensor, etc.); or one or more other sensors configured to receive physiologic information of the subject.

Traditional cardiac rhythm management (CRM) devices, such as pacemakers, defibrillators, or cardiac resynchronizers, include subcutaneous devices configured to be implanted in a chest of a subject, having one or more leads to position one or more electrodes or other sensors at various locations in or near the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the subject.

Implantable devices can additionally include leadless cardiac pacemakers (LCP), small (e.g., smaller than traditional implantable CRM devices, in certain examples having a volume of about 1 cc, etc.), self-contained devices including one or more sensors, circuits, or electrodes configured to monitor physiologic information (e.g., heart rate, etc.) from, detect physiologic conditions (e.g., tachycardia) associated with, or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the subject without required implant or an in-patient procedure for placement, battery replacement, or repair. However, such sensors and devices, in contrast to implantable medical devices, may have reduced patient compliance, increased detection noise, or reduced detection sensitivity.

For each ambulatory medical device (AMD) described above (e.g., implantable medical device (IMD) or wearable medical devices (WMD), each additional sensor can increase system cost and complexity, reduce system reliability, or increase the power consumption and reduce the usable life of the ambulatory device. Accordingly, it can be beneficial to use a single sensor to determine multiple types of physiologic information, or a smaller number of sensors to measure a larger number of different types of physiologic information.

In an example, an accelerometer, microphone, or acoustic sensor can sense or detect acceleration information of the subject including or indicative of cardiac acceleration information (e.g., heart sound information, such as from pressure waveforms due to cardiac vibrations; endocardial acceleration information, such as from acceleration information detected on or within a cardiac chamber; cardiac vibration information; etc.) of the subject. In certain examples, the same or different accelerometer, microphone, acoustic sensor or one or more other activity, posture, or exertion sensors can receive exertion information (e.g., activity information, posture information, etc.) of the subject. Exertion information can include physical activity information of the subject occurring at a different frequency than cardiac acceleration information. Accordingly, the sampling rate to detect physical activity information of the subject is often much lower than that required to detect cardiac acceleration information (e.g., exertion is often detected at a sampling rate of 50 Hz or less, whereas cardiac acceleration information is often detected at a sampling rate of 1 kHz or higher).

In an example, a single sensor can detect acceleration information at a detection period and sampling rate such that both cardiac acceleration information and exertional information can be determined from the detected acceleration information over the same or overlapping time periods. However, such determination of the separate cardiac acceleration information and the exertion information from the same acceleration information can require substantial processing time and resources. Accordingly, when a single sensor is used to detect cardiac acceleration information and exertion information, the cardiac acceleration information and the exertion information are more often detected in non-overlapping time periods (e.g., the single sensor detects one of the cardiac acceleration information or the exertional information at a time) at different sampling rates and with different pre-processing (e.g., filters, signal conditioning, etc.), such as to reduce the processing resources required to sense and process the separate information in the AMD or medical-device system having limited or different storage, processing, power, and performance capabilities.

In other examples, different sensors (or a single sensor with different physical sensing portions or components) can be used to detect the cardiac acceleration information and the exertion information. For example, it can be advantageous to detect physical activity or exertion information using a more rigid sensor tuned to sense activity having a higher magnitude and lower frequency response than cardiac acceleration information; whereas it can be advantageous to detect cardiac acceleration information using sensor having higher sensitivity and sampling frequency (e.g., a microphone instead of an accelerometer, etc.). In certain examples, separate axes of a multi-axis sensor can be used to detect different information at different sampling rates.

Figure 7:
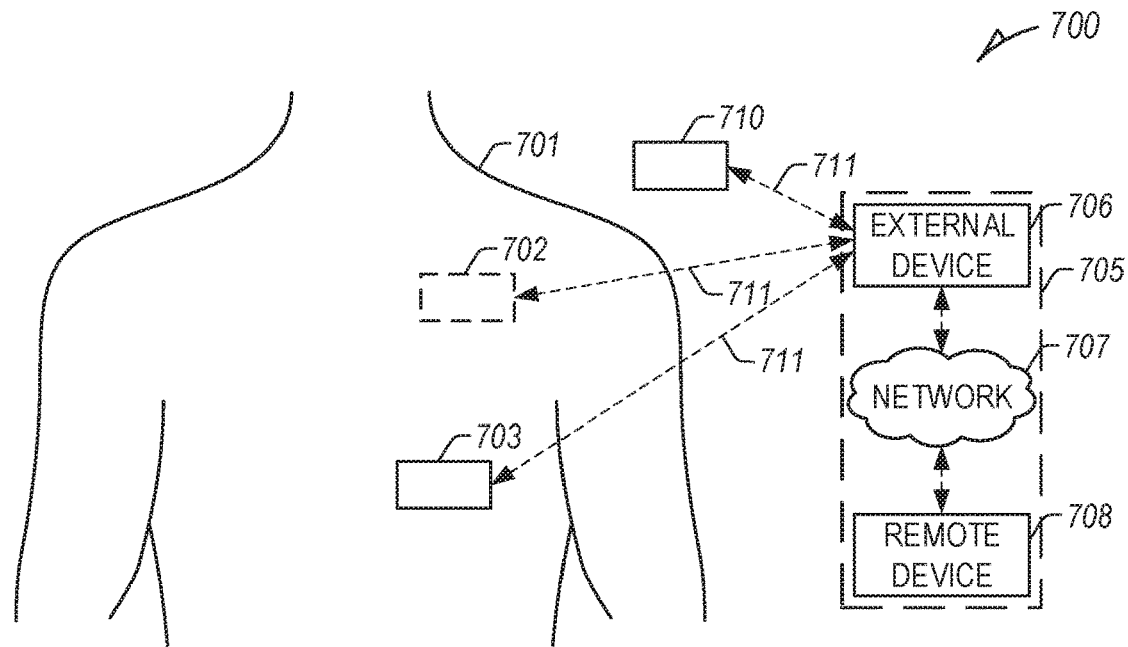
FIG. 7 illustrates an example patient management system and portions of an environment in which the system may operate.

FIG. 7 illustrates an example patient management system 700 and portions of an environment in which the system 700 may operate. The patient management system 700 can perform a range of activities, including remote patient monitoring and diagnosis of a disease condition. Such activities can be performed proximal to a patient 701, such as in a patient home or office, through a centralized server, such as in a hospital, clinic, or physician office, or through a remote workstation, such as a secure wireless mobile computing device.

The patient management system 700 can include one or more ambulatory devices, an external system 705, and a communication link 711 providing for communication between the one or more ambulatory devices and the external system 705. The one or more ambulatory devices can include an implantable medical device (IMD) 702, a wearable medical device 703, or one or more other implantable, leadless, subcutaneous, external, wearable, or ambulatory medical devices configured to monitor, sense, or detect information from, determine physiologic information about, or provide one or more therapies to treat various cardiac conditions of the patient 701, such as high blood pressure, an ability of a heart to sufficiently deliver blood to a body, including atrial fibrillation (AF), congestive heart failure (CHF), hypertension, or one or more other cardiac or non-cardiac conditions (e.g., dehydration, hemorrhage, renal dysfunction, etc.).

In an example, the IMD 702 can include one or more traditional cardiac rhythm management (CRM) devices, such as a pacemaker or defibrillator, implanted in a chest of a subject, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the subject 701. In another example, the IMD 702 can include a monitor implanted, for example, subcutaneously in the chest of subject 701.

The IMD 702 can include an assessment circuit configured to detect or determine specific physiologic information of the subject 701, or to determine one or more conditions or provide information or an alert to a user, such as the subject 701 (e.g., a patient), a clinician, or one or more other caregivers. The IMD 702 can alternatively or additionally be configured as a therapeutic device configured to treat one or more medical conditions of the subject 701. The therapy can be delivered to the subject 701 via the lead system and associated electrodes or using one or more other delivery mechanisms. The therapy can include anti-arrhythmic therapy to treat an arrhythmia or to treat or control one or more complications from arrhythmias, such as syncope, congestive heart failure (CHF), or stroke, among others. In other examples, the therapy can include delivery of one or more drugs to the subject 701 using the IMD 702 or one or more of the other ambulatory devices. Examples of the anti-arrhythmic therapy include pacing, cardioversion, defibrillation, neuromodulation, drug therapies, or biological therapies, among other types of therapies. In other examples, therapies can include cardiac resynchronization therapy (CRT) for rectifying dyssynchrony and improving cardiac function in CHF patients. In some examples, the IMD 702 can include a drug delivery system, such as a drug infusion pump to deliver drugs to the patient for managing arrhythmias or complications from arrhythmias, hypertension, or one or more other physiologic conditions. In yet other examples, the IMD 702 can include a therapy circuit or module configured to treat hypertension (e.g., a neurostimulation therapy circuit, a drug delivery therapy circuit, a stimulation therapy circuit, etc.).

The wearable medical device 703 can include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.). The wearable medical device 703 can include an optical sensor configured to detect a photoplethysmogram (PPG) signal on a wrist, finger, or other location on the subject 701. In other examples, the wearable medical device 703 can include an acoustic sensor or accelerometer to detect acoustic information (e.g., heart sounds) or the sound or vibration of blood flow, an impedance sensor to detect impedance variations associated with changes in blood flow or volume, a temperature sensor to detect temperature variation associated with blood flow, a laser Doppler vibrometer or other pressure, strain, or physical sensor to detect physical variations associated with blood flow, etc.

The patient management system 700 can include, among other things, a respiration sensor configured to receive respiration information (e.g., a respiration rate (RR), a respiration volume (tidal volume), etc.), a heart sound sensor configured to receive heart sound information, a thoracic impedance sensor configured to receive impedance information, a cardiac sensor configured to receive cardiac electrical information, an activity sensor configured to receive information about a physical motion (e.g., activity, posture, etc.), a plethysmography sensor, or one or more other sensors configured to receive physiologic information of the subject 701.

The external system 705 can include a dedicated hardware/software system, such as a programmer, a remote server-based patient management system, or alternatively a system defined predominantly by software running on a standard personal computer. The external system 705 can manage the subject 701 through the IMD 702 or one or more other ambulatory devices connected to the external system 705 via a communication link 711. In other examples, the IMD 702 can be connected to the wearable device 703, or the wearable device 703 can be connected to the external system 705, via the communication link 711. This can include, for example, programming the IMD 702 to perform one or more of acquiring physiological data, performing at least one self-diagnostic test (such as for a device operational status), analyzing the physiological data to detect a cardiac arrhythmia, or optionally delivering or adjusting a therapy to the subject 701. Additionally, the external system 705 can send information to, or receive information from, the IMD 702 or the wearable device 703 via the communication link 711. Examples of the information can include real-time or stored physiological data from the subject 701, diagnostic data, such as detection of cardiac arrhythmias or events of worsening heart failure, responses to therapies delivered to the subject 701, or device operational status of the IMD 702 or the wearable device 703 (e.g., battery status, lead impedance, etc.). The communication link 711 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

By way of example and not limitation, the external system 705 can include an external device 706 in proximity of the one or more ambulatory devices, and a remote device 708 in a location relatively distant from the one or more ambulatory devices, in communication with the external device 706 via a communication network 707. Examples of the external device 706 can include a medical device programmer.

The remote device 708 can be configured to evaluate collected subject or patient information and provide alert notifications, among other possible functions. In an example, the remote device 708 can include a centralized server acting as a central hub for collected data storage and analysis. The server can be configured as a uni-, multi-, or distributed computing and processing system. The remote device 708 can receive data from multiple subjects or patients. The data can be collected by the one or more ambulatory devices, among other data acquisition sensors or devices associated with the subject 701. The server can include a memory device to store the data in a patient database. The server can include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory devices, such as the IMD. By way of example, alert notifications can include a Web page update, phone or pager call, E-mail, SMS, text or "Instant" message, as well as a message to the subject or patient and a simultaneous direct notification to emergency services and to the clinician. Other alert notifications are possible. The server can include an alert prioritizer circuit configured to prioritize the alert notifications. For example, an alert of a detected medical event can be prioritized using a similarity metric between the physiological data associated with the detected medical event to physiological data associated with the historical alerts.

The remote device 708 may additionally include one or more locally configured clients or remote clients securely connected over the communication network 707 to the server. Examples of the clients can include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 708, including the server and the interconnected clients, may also execute a follow-up scheme by sending follow-up requests to the one or more ambulatory devices, or by sending a message or other communication to the subject 701 (e.g., the patient), clinician or authorized third party as a compliance notification.

The communication network 707 can provide wired or wireless interconnectivity. In an example, the communication network 707 can be based on the Transmission Control Protocol/Internet Protocol (TCP/IP) network communication specification, although other types or combinations of networking implementations are possible. Similarly, other network topologies and arrangements are possible.

One or more of the external device 706 or the remote device 708 can output the detected medical events to a system user, such as the patient or a clinician, or to a process including, for example, an instance of a computer program executable in a microprocessor. In an example, the process can include an automated generation of recommendations for anti-arrhythmic therapy, or a recommendation for further diagnostic test or treatment. In an example, the external device 706 or the remote device 708 can include a respective display unit for displaying the physiological or functional signals, or alerts, alarms, emergency calls, or other forms of warnings to signal the detection of arrhythmias. In some examples, the external system 705 can include an external data processor configured to analyze the physiological or functional signals received by the one or more ambulatory devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory devices or the external system 705 can be implemented using hardware, software, firmware, or combinations thereof. Portions of the one or more ambulatory devices or the external system 705 can be implemented using an application-specific circuit that can be constructed or configured to perform one or more functions or can be implemented using a general-purpose circuit that can be programmed or otherwise configured to perform one or more functions. Such a general-purpose circuit can include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" can include electronic circuits configured to receive information and provide an electronic output representative of such received information.

The patient management system 700 can include a therapy device (e.g., a therapy circuit 709, etc.), such as a drug delivery device configured to provide therapy or therapy information (e.g., dosage information, etc.) to the subject 701, such as using information from one or more of the ambulatory devices. In other examples, one or more of the ambulatory devices can be configured to provide therapy or therapy information to the subject 701. The therapy device can be configured to send information to or receive information from one or more of the ambulatory devices or the external system 705 using the communication link 711. In an example, the one or more ambulatory devices, the external device 706, or the remote device 708 can be configured to control one or more parameters of the therapy device 710.

The patient management system 700 can include a patient chronic condition-based HF assessment circuit, such as illustrated in the commonly assigned Qi An et al. U.S. application Ser. No. 14/510,392, titled "Methods and Apparatus for Detecting Heart Failure Decompensation Event and Stratifying the Risk of the Same", herein incorporated by reference in its entirety. The patient chronic condition-based HF assessment circuit can include a signal analyzer circuit and a risk stratification circuit. The signal analyzer circuit can receive patient chronic condition indicators and one or more physiologic signals from a patient and select one or more patient-specific sensor signals or signal metrics from the physiologic signals. The signal analyzer circuit can receive the physiologic signals from the patient using the electrodes on one or more of the leads, or physiologic sensors deployed on or within the patient and communicated with one or more other components of the patient management system 700. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 705 can allow for programming the one or more ambulatory devices and can receives information about one or more signals acquired by the one or more ambulatory devices, such as can be received via a communication link 711. The external system 705 can include a local external IMD programmer. The external system 705 can include a remote patient management system that can monitor patient status or adjust one or more therapies such as from a remote location.

The patient chronic condition-based HF assessment circuit, or other assessment circuit, may be implemented at the external system 705, which can be configured to perform HF risk stratification such as using data extracted from the one or more ambulatory devices or data stored in a memory within the external system 705. Portions of patient chronic condition-based HF or other assessment circuit may be distributed between the one or more ambulatory devices and the external system 705.

Figure 8:
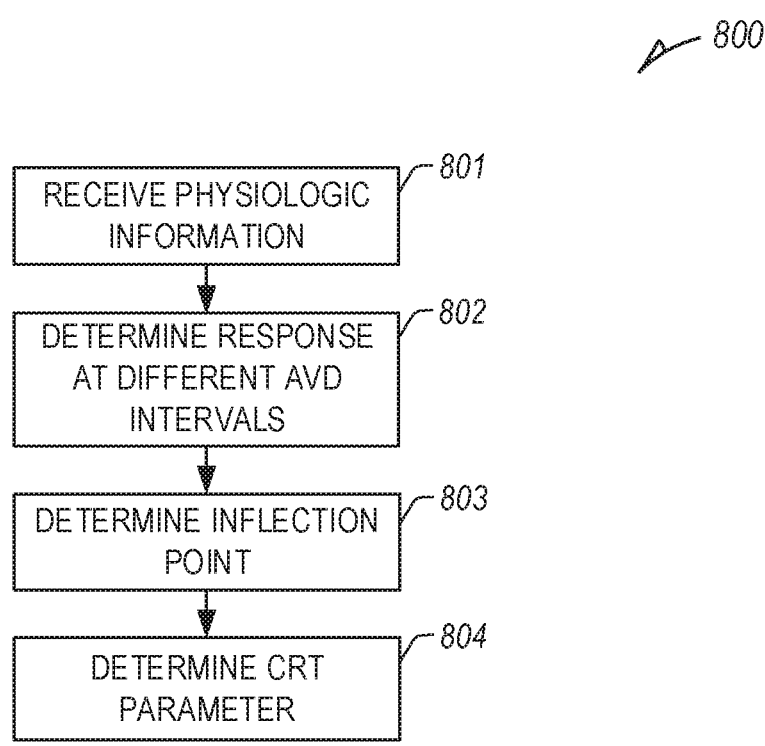
FIG. 8 illustrates an example method of determining one or more CRT parameters.

FIG. 8 illustrates an example method 800 of determining one or more CRT parameters for a subject using, among other things, a determined inflection point of a determined response across a set of stimulation signals at different AVD intervals.

At 801, physiologic information can be received from a subject, such as using a signal receiver circuit. The physiologic information can include cardiac electrical information (e.g., ECG information, or electrical information of a heart of the subject, etc.), cardiac acceleration information (e.g., heart sounds, etc.), one or more other type of physiologic information of the subject, or combinations or permutations thereof. In an example, the signal receiver circuit can receive sensor information and determine one or more parameters, or can receive already determined parameters, such as from one or more other circuits or processes. In an example, the physiologic information can include information received in response to a set of stimulation signals provided to the subject at different AVD intervals.

At 802, a response can be determined, such as using an assessment circuit. The response can be determined for different AVD intervals, such as across the set of stimulation signals at the different AVD intervals. In an example, the response can include a time period between two or more physiologic events, including at least one of a cardiac acceleration event (e.g., a heart sound event). In an example, the heart sound event can include a time (e.g., an onset time) of an S1, an S2, or one or more other heart sound event. The response can include a time between the heart sound event and one or more other events, such as a time of a cardiac electrical event, such as a P wave, etc. In an example, the determined response can include a P-S1 response at the different AVD intervals, a P-S2 response at the different AVD intervals, etc. In other examples, the determined response can include a response between two or more physiologic events or parameters, a change in amplitude of one or more physiologic events or parameters, etc.

At 803, an inflection point of the response can be determined, such as using the assessment circuit. The inflection point can be determined using a threshold, such as a measurement threshold to account for error or variation, and a value of the response at the largest AVD, such as illustrated in FIG. 2, etc. In other examples, the inflection point can be determined using the shape of the response, such as using a rate of change in response with increasing AVD. In certain examples, the shape of the response can be used to determine the inflection point, such as a declining rate of change, etc.

At 804, a CRT parameter can be determined using the inflection point. In certain examples, the CRT parameter can include an AVD for subsequent CRT therapy or stimulation at or near the determined inflection point.

The method 800 can be implemented in a clinical setting under direction of a physician or other caregiver, or in an ambulatory setting, such as on a fixed schedule or triggered by a change of sensor information (e.g., impedance, activity, HS, RV-LV, or one or more other parameter, indication, or stratifier, etc.). For example, if a worsening condition is detected, such as worsening heart failure, etc., one or more therapy device settings, e.g., CRT parameters, can be re-optimized in response, etc.

Figure 9:
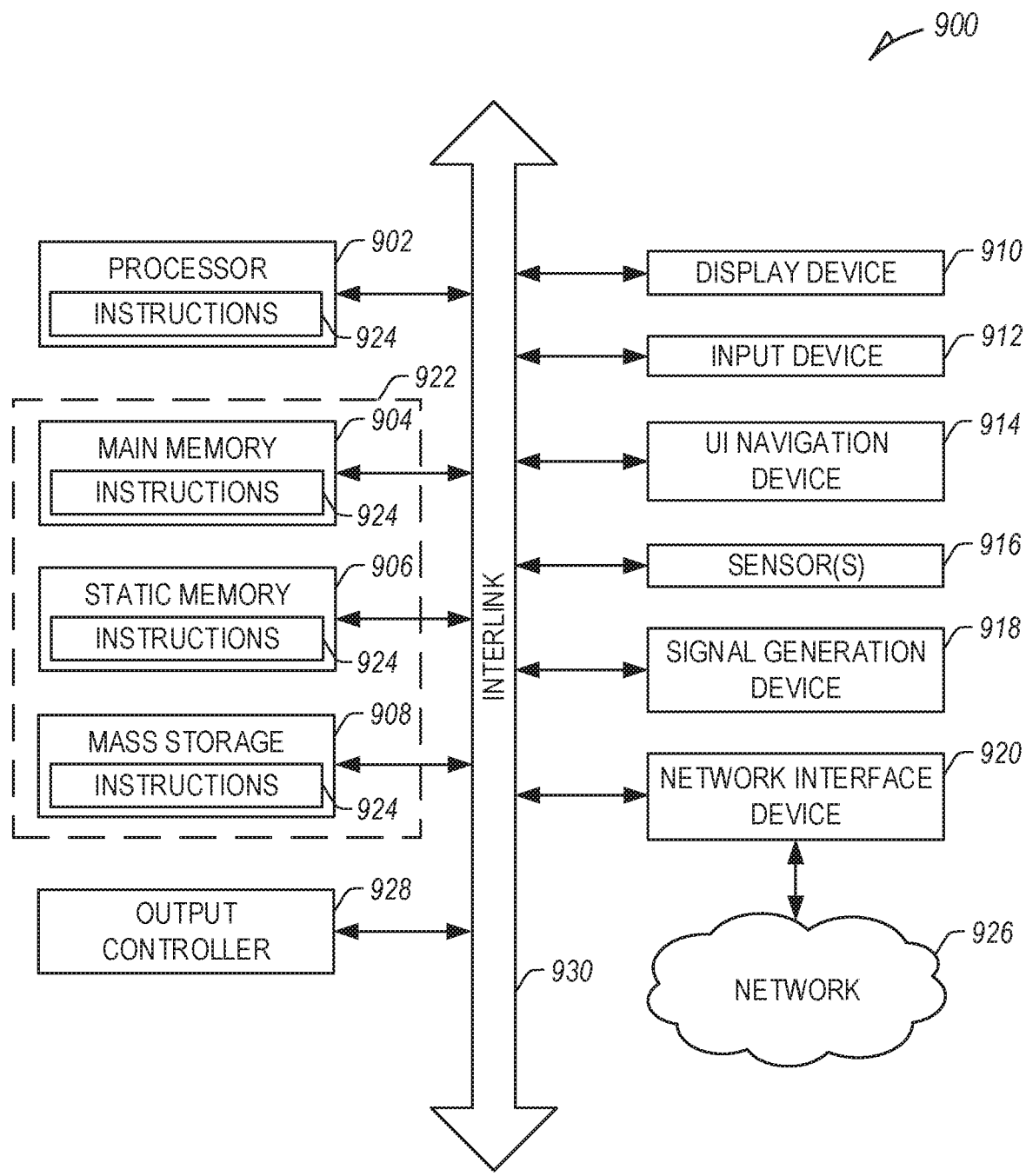
FIG. 9 illustrates a block diagram of an example machine upon which any one or more of the techniques discussed herein may perform.

FIG. 9 illustrates a block diagram of an example machine 900 upon which any one or more of the techniques (e.g., methodologies) discussed herein may perform. Portions of this description may apply to the computing framework of one or more of the medical devices described herein, such as the IMD, the external programmer, etc. Further, as described herein with respect to medical device components, systems, or machines, such may require regulatory-compliance not capable by generic computers, components, or machinery.

Examples, as described herein, may include, or may operate by, logic or a number of components, or mechanisms in the machine 900. Circuitry (e.g., processing circuitry) is a collection of circuits implemented in tangible entities of the machine 900 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 900 follow.

In alternative embodiments, the machine 900 may operate as a standalone device or may be connected (e.g., networked) to other machines. In a networked deployment, the machine 900 may operate in the capacity of a server machine, a client machine, or both in server-client network environments. In an example, the machine 900 may act as a peer machine in peer-to-peer (P2P) (or other distributed) network environment. The machine 900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 900 may include a hardware processor 902 (e.g., a central processing unit (CPU), a graphics processing unit (GPU), a hardware processor core, or any combination thereof), a main memory 904, a static memory (e.g., memory or storage for firmware, microcode, a basic-input-output (BIOS), unified extensible firmware interface (UEFI), etc.) 906, and mass storage 908 (e.g., hard drive, tape drive, flash storage, or other block devices) some or all of which may communicate with each other via an interlink (e.g., bus) 930. The machine 900 may further include a display unit 910, an alphanumeric input device 912 (e.g., a keyboard), and a user interface (UI) navigation device 914 (e.g., a mouse). In an example, the display unit 910, input device 912, and UI navigation device 914 may be a touch screen display. The machine 900 may additionally include a signal generation device 918 (e.g., a speaker), a network interface device 920, and one or more sensors 916, such as a global positioning system (GPS) sensor, compass, accelerometer, or one or more other sensors. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 902, the main memory 904, the static memory 906, or the mass storage 908 may be, or include, a machine-readable medium 922 on which is stored one or more sets of data structures or instructions 924 (e.g., software) embodying or utilized by any one or more of the techniques or functions described herein. The instructions 924 may also reside, completely or at least partially, within any of registers of the processor 902, the main memory 904, the static memory 906, or the mass storage 908 during execution thereof by the machine 900. In an example, one or any combination of the hardware processor 902, the main memory 904, the static memory 906, or the mass storage 908 may constitute the machine-readable medium 922. While the machine-readable medium 922 is illustrated as a single medium, the term "machine-readable medium" may include a single medium or multiple media (e.g., a centralized or distributed database, and/or associated caches and servers) configured to store the one or more instructions 924.

The term "machine-readable medium" may include any medium that is capable of storing, encoding, or carrying instructions for execution by the machine 900 and that cause the machine 900 to perform any one or more of the techniques of the present disclosure, or that is capable of storing, encoding, or carrying data structures used by or associated with such instructions. Non-limiting machine-readable medium examples may include solid-state memories, optical media, magnetic media, and signals (e.g., radio frequency signals, other photon-based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may be further transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 900, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments.

Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system, comprising:
a signal receiver circuit configured to receive cardiac electrical information of a subject and cardiac acceleration information of the subject in response to a set of stimulation signals at different atrioventricular delay (AVD) intervals; and
an assessment circuit configured to:
determine a response between the received cardiac electrical information and the received cardiac acceleration information across the set of stimulation signals at the different AVD intervals;
determine an inflection point of the determined response where the determined response approaches within a measurement error of, or overtakes, an intrinsic response; and
determine a cardiac resynchronization therapy (CRT) parameter for the subject using the determined inflection point.

2. The system of claim 1, wherein the set of stimulation signals at different AVD intervals includes at least three stimulation signals at different AVD intervals in separate cardiac cycles.

3. The system of claim 1, wherein the system is a medical-device system, comprising:
a cardiac stimulation circuit configured to generate the set of stimulation signals to be delivered to the subject, the stimulation signal including a left ventricular (LV) stimulation signal at an AVD interval; and
a stimulation control circuit configured to adjust the AVD interval of the set of stimulation signals across different cardiac cycles,
wherein the assessment circuit is configured to determine the inflection point using the determined response across the set of stimulation signals at the different AVD intervals and a threshold.

4. The system of claim 1, wherein the assessment circuit is configured to determine the inflection point using a characteristic of the determined response.

5. The system of claim 1, comprising:
multiple electrodes configured to provide stimulation to a heart of the subject using the stimulation signal from the cardiac stimulation circuit and to detect the cardiac electrical information of the subject; and
an accelerometer configured to detect the cardiac acceleration information of the subject,
wherein the signal receiver circuit is configured to receive the cardiac electrical information from at least two of the multiple electrodes and the cardiac acceleration information from the accelerometer.

6. The system of claim 1, wherein the received cardiac electrical information includes a time of a P wave of the subject,
wherein the received cardiac acceleration information includes a time of a heart sound of the subject,
wherein the assessment circuit is configured to determine the response between the time of the P wave and the time of the heart sound, and
wherein, to determine the CRT parameter using the determined inflection point, the assessment circuit is configured to determine an AVD value at the determined inflection point.

7. The system of claim 6, wherein the time of the heart sound includes a time of a first heart sound (S1), and
wherein the assessment circuit is configured to determine the response between the time of the P wave and the time of the S1 (P-S1).

8. The system of claim 6, wherein the time of the heart sound includes a time of a second heart sound (S2), and
wherein the assessment circuit is configured to determine the response between the time of the P wave and the time of the S2 (P-S2).

9. The system of claim 1, wherein the CRT parameter includes an AVD.

10. The system of claim 1, wherein the assessment circuit is configured to determine the CRT parameter using the determined inflection point and at least one of a determined QRS width or one or more of an interval between an atrial activation and a right ventricular activation (ARV) or an interval between an atrial activation and a left ventricular activation (ALV).

11. The system of claim 1, wherein, to determine the response, the assessment circuit is configured to determine a response curve between the received cardiac electrical information and the received cardiac acceleration information across the set of stimulation signals at the different AVD intervals,
wherein the assessment circuit is configured to determine the inflection point where the determined response approaches within a measurement error or overtakes an intrinsic response using a shape of the response curve, and
wherein the different AVD intervals including a range of AVD intervals for the patient.

12. A method, comprising:
receiving, using a signal receiver circuit, cardiac electrical information of a subject and cardiac acceleration information of the subject in response to a set of stimulation signals at different atrioventricular delay (AVD) intervals;
determining, using an assessment circuit, a response between the received cardiac electrical information and the received cardiac acceleration information across the set of stimulation signals at the different AVD intervals;
determining, using the assessment circuit, an inflection point of the determined response where the determined response approaches within a measurement error of, or overtakes, an intrinsic response; and
determining, using the assessment circuit, a cardiac resynchronization therapy (CRT) parameter for the subject using the determined inflection point.

13. The method of claim 12, wherein the set of stimulation signals at different AVD intervals includes at least three stimulation signals at different AVD intervals in separate cardiac cycles.

14. The method of claim 12, comprising:
generating, using a cardiac stimulation circuit, the set of stimulation signals to be delivered to the subject, the stimulation signal including a left ventricular (LV) stimulation signal at an AVD interval; and
adjusting, using a stimulation control circuit, the AVD interval of the set of stimulation signals across different cardiac cycles,
wherein determining the inflection point comprises using the response curve across the set of stimulation signals at the different AVD intervals and a threshold.

15. The method of claim 12, comprising:
providing, using multiple electrodes, stimulation to a heart of the subject using the stimulation signal from the cardiac stimulation circuit;
detecting, using at least two of the multiple electrodes, cardiac electrical information of the subject; and
detecting, using an accelerometer, the cardiac acceleration information of the subject,
wherein receiving the cardiac electrical information comprises from at least two of the multiple electrodes and receiving the cardiac acceleration information comprises from the accelerometer.

16. The method of claim 12, wherein determining the response between the received cardiac electrical information and the received cardiac acceleration information comprises determining a response between a time of a P wave and a time of a heart sound, and
wherein, to determine the CRT parameter using the determined inflection point, the assessment circuit is configured to determine an AVD value at the determined inflection point.

17. The method of claim 16, wherein the time of the heart sound includes a time of a first heart sound (S1), and the response includes a response between the time of the P wave and the time of the S1 (P-S1).

18. The method of claim 16, wherein the time of the heart sound includes a time of a second heart sound (S2), and the response includes a response between the time of the P wave and the time of the S2 (P-S2).

19. The method of claim 12, wherein the CRT parameter includes an AVD.

20. The method of claim 12, wherein determining the CRT parameter includes using the determined inflection point and at least one of a determined QRS width or one or more of an interval between an atrial activation and a right ventricular activation (ARV) or an interval between an atrial activation and a left ventricular activation (ALV).

* * * * *